(12) United States Patent
Koifman et al.

(10) Patent No.: US 10,653,483 B2
(45) Date of Patent: May 19, 2020

(54) RECONFIGURABLE HANDHELD LASER TREATMENT SYSTEMS AND METHODS

(71) Applicant: LUMENIS LTD., Yokneam Ilit (IL)

(72) Inventors: Igal Koifman, Hadera (IL); Uri Voitsechov, Moshav Amirim (IL)

(73) Assignee: LUMENIS LTD (IL)

( * ) Notice: Subject to any disclaimer, the term of this patent is extended or adjusted under 35 U.S.C. 154(b) by 56 days.

(21) Appl. No.: 15/352,634

(22) Filed: Nov. 16, 2016

(65) Prior Publication Data
US 2017/0056110 A1 Mar. 2, 2017

Related U.S. Application Data

(63) Continuation of application No. 14/736,300, filed on Jun. 11, 2015, now Pat. No. 9,526,578, which is a
(Continued)

(51) Int. Cl.
*A61B 18/20* (2006.01)
*A61N 5/06* (2006.01)
(Continued)

(52) U.S. Cl.
CPC ............ *A61B 18/20* (2013.01); *A61B 18/201* (2013.01); *A61B 18/203* (2013.01); *A61B 90/98* (2016.02); *A61N 5/06* (2013.01); *A61N 5/0617* (2013.01); *A61B 2018/00005* (2013.01); *A61B 2018/00172* (2013.01); *A61B 2018/00291* (2013.01); *A61B 2018/00452* (2013.01);
(Continued)

(58) Field of Classification Search
CPC .................................. A61B 18/18; A61B 17/20
USPC ...................... 606/1, 3, 9, 10, 13, 19; 604/22
See application file for complete search history.

(56) References Cited

U.S. PATENT DOCUMENTS 5,100,417 A 3/1992 Cerier et al.
5,344,418 A * 9/1994 Ghaffari ............... A61B 18/203
606/13
(Continued)

FOREIGN PATENT DOCUMENTS

EP 1627662 2/2006
WO WO89/0871 2/1989
(Continued)

*Primary Examiner* — Michael W Kahelin
*Assistant Examiner* — Shirley X Jian
(74) *Attorney, Agent, or Firm* — ISUS Intellectual Property

(57) ABSTRACT

In one embodiment, a handheld laser treatment apparatus comprises: a handset including a treatment chamber, the treatment chamber having an open treatment aperture; a laser array arranged to project optical energy into the treatment chamber and coupled to a power source; at least one vacuum channel positioned within the treatment chamber and coupled to a vacuum source; a trigger sensor coupled to logic that controls activation of the laser array and the vacuum channel; an attachment sensor arranged to detect which of a plurality of attachments are inserted into the treatment chamber through the treatment aperture. The logic enables activation of the vacuum channel when the attachment sensor detects a first attachment of the plurality of attachments inserted into the treatment aperture. The logic disables activation of the vacuum channel when the attachment sensor detects a second attachment of the plurality of attachments inserted into the treatment aperture.

8 Claims, 17 Drawing Sheets

Related U.S. Application Data continuation of application No. 13/413,826, filed on Mar. 7, 2012, now Pat. No. 9,149,332, which is a continuation-in-part of application No. 13/363,570, filed on Feb. 1, 2012, now Pat. No. 9,078,681.

(51) Int. Cl.
*A61B 90/98* (2016.01)
*A61N 5/067* (2006.01)
*A61B 18/00* (2006.01)

(52) U.S. Cl.
CPC ........... *A61B 2018/00476* (2013.01); *A61B 2018/00666* (2013.01); *A61B 2018/00898* (2013.01); *A61B 2018/00928* (2013.01); *A61B 2018/00988* (2013.01); *A61B 2018/20361* (2017.05); *A61B 2018/205547* (2017.05); *A61N 2005/067* (2013.01); *A61N 2005/0644* (2013.01)

(56) References Cited

U.S. PATENT DOCUMENTS

| | | | |
|---|---|---|---|
| 5,707,368 A * | 1/1998 | Cozean | A61B 18/22 606/15 |
| 5,728,090 A * | 3/1998 | Martin | A61N 5/0601 606/11 |
| 6,056,738 A | 5/2000 | Marchitto et al. | |
| D443,059 S | 5/2001 | Endo | |
| 6,310,901 B1 | 10/2001 | Mahmoudi et al. | |
| D453,829 S | 2/2002 | McMahon et al. | |
| 6,454,763 B1 | 9/2002 | Motter et al. | |
| 6,458,094 B1 | 10/2002 | McMahon et al. | |
| 6,706,035 B2 | 3/2004 | Cense et al. | |
| 6,758,845 B1 | 7/2004 | Weckwerth et al. | |
| 6,942,658 B1 | 9/2005 | Rizoiu et al. | |
| 7,022,121 B2 * | 4/2006 | Stern | A61B 18/14 606/41 |
| 7,033,350 B2 * | 4/2006 | Bahk | A61B 18/20 606/10 |
| 7,204,832 B2 * | 4/2007 | Altshuler | A45D 26/0061 606/22 |
| 7,232,450 B2 | 6/2007 | Gorans et al. | |
| 7,270,657 B2 | 9/2007 | Rizoiu et al. | |
| 7,384,419 B2 | 6/2008 | Jones et al. | |
| D581,050 S | 11/2008 | Cottier | |
| D608,881 S | 1/2010 | Ramstad et al. | |
| 10,448,998 B2 * | 10/2019 | Levy | A61N 5/0616 |
| 2002/0081080 A1 | 6/2002 | Balle-Petersen et al. | |
| 2002/0151887 A1 | 10/2002 | Stern et al. | |
| 2004/0030325 A1 | 2/2004 | Cahir et al. | |
| 2005/0154381 A1 * | 7/2005 | Altshuler | A61B 18/203 606/9 |
| 2006/0095096 A1 | 5/2006 | DeBenedictis et al. | |
| 2006/0122585 A1 | 6/2006 | Connors et al. | |
| 2006/0189964 A1 | 8/2006 | Anderson et al. | |
| 2007/0016074 A1 | 1/2007 | Abreu | |
| 2007/0106284 A1 * | 5/2007 | Siegel | A61B 18/203 606/15 |
| 2007/0179482 A1 | 8/2007 | Anderson | |
| 2008/0119830 A1 | 5/2008 | Ramstad et al. | |
| 2008/0161783 A1 | 7/2008 | Cao | |
| 2008/0215039 A1 | 9/2008 | Slatkine et al. | |
| 2008/0281254 A1 | 11/2008 | Humayun et al. | |
| 2008/0281301 A1 | 11/2008 | DeBoer et al. | |
| 2012/0226268 A1 | 9/2012 | Liu et al. | |
| 2013/0150841 A1 | 6/2013 | Schomacker et al. | |
| 2015/0017599 A1 * | 1/2015 | Marincek | A61N 5/0603 433/29 |
| 2016/0213427 A1 * | 7/2016 | Levy | A61B 18/203 |
| 2017/0273744 A1 * | 9/2017 | Koifman | A61B 18/203 |

FOREIGN PATENT DOCUMENTS

| | | |
|---|---|---|
| WO | 0134048 | 5/2001 |
| WO | 2006012752 | 2/2006 |
| WO | 2006031632 | 3/2006 |

* cited by examiner

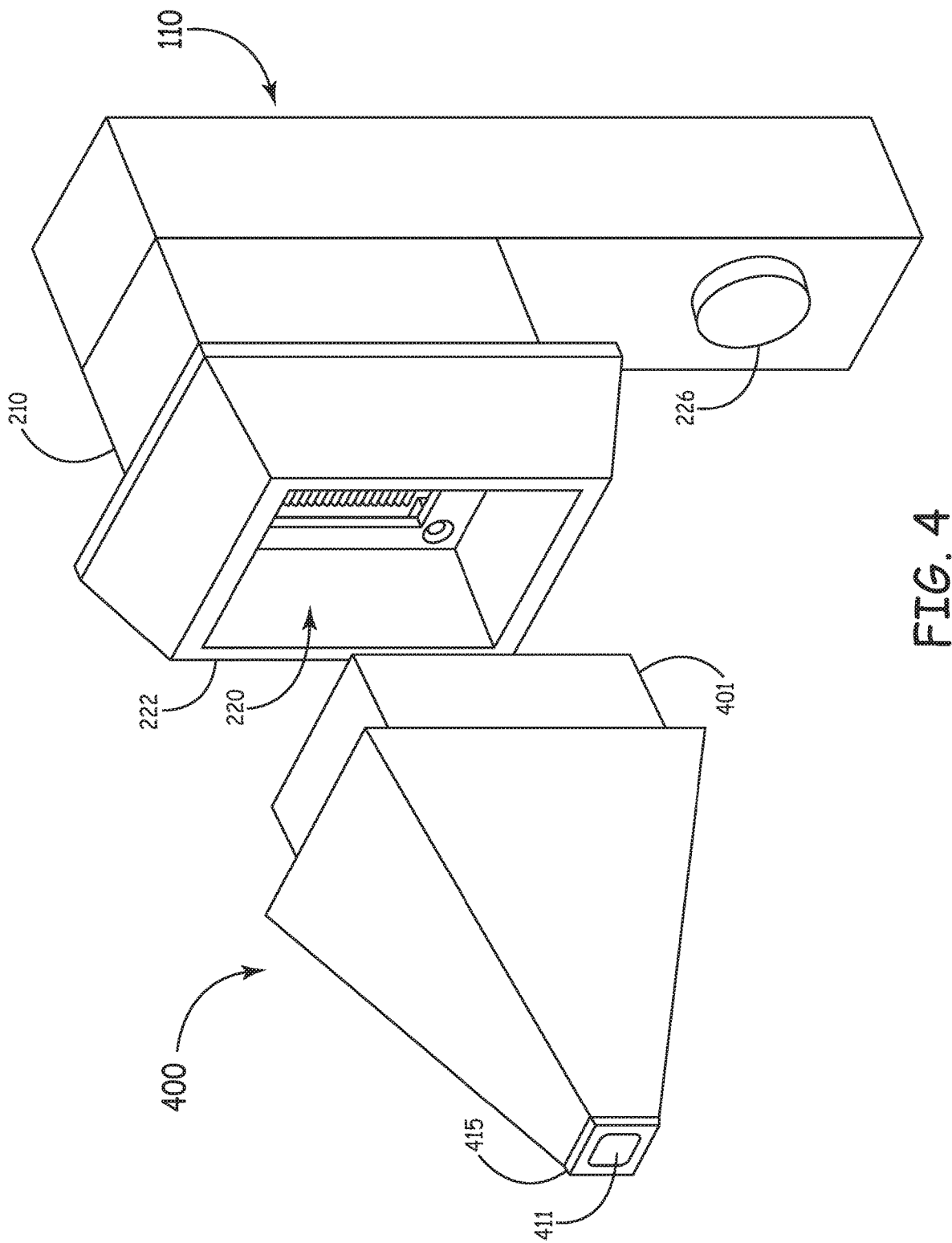

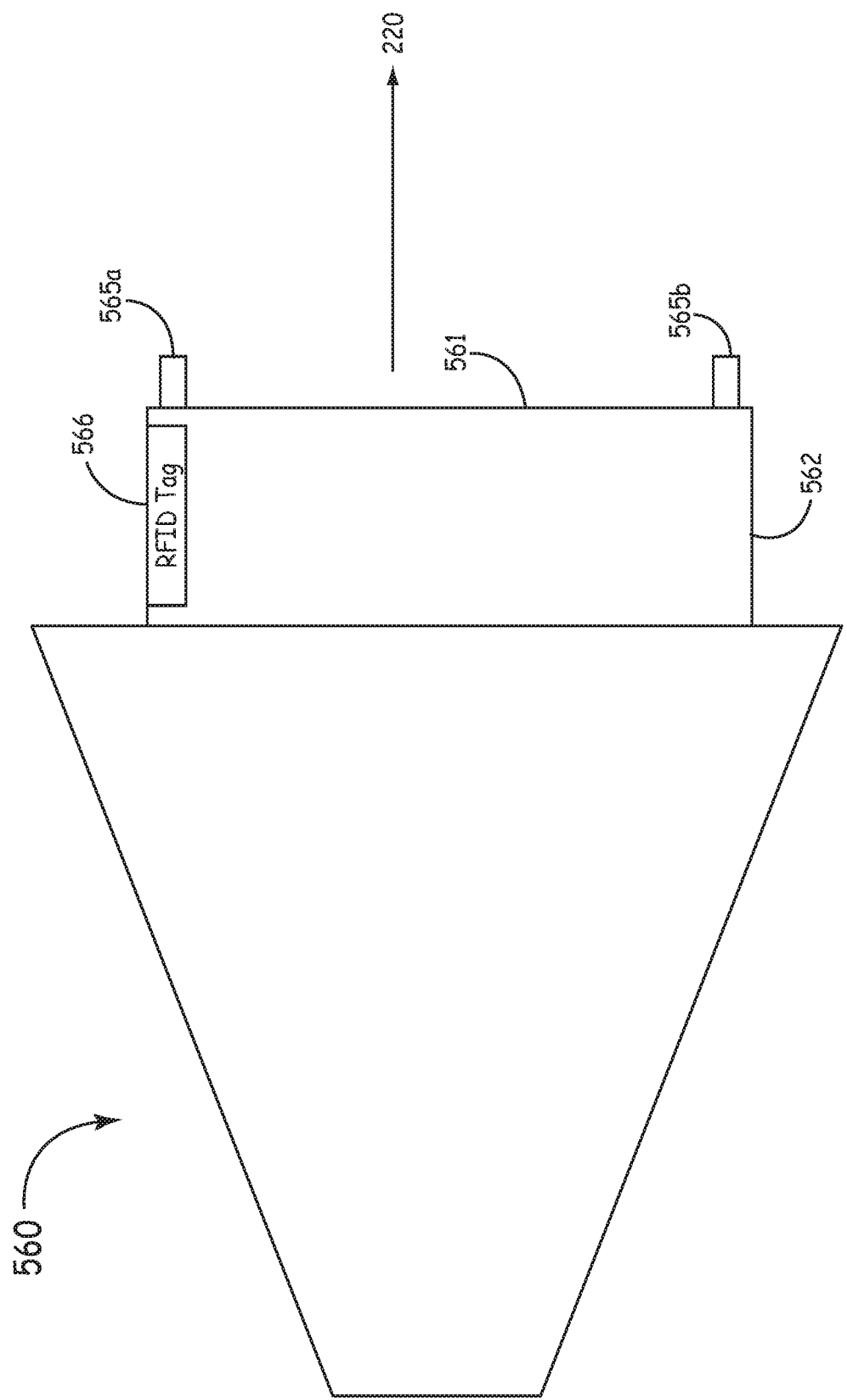

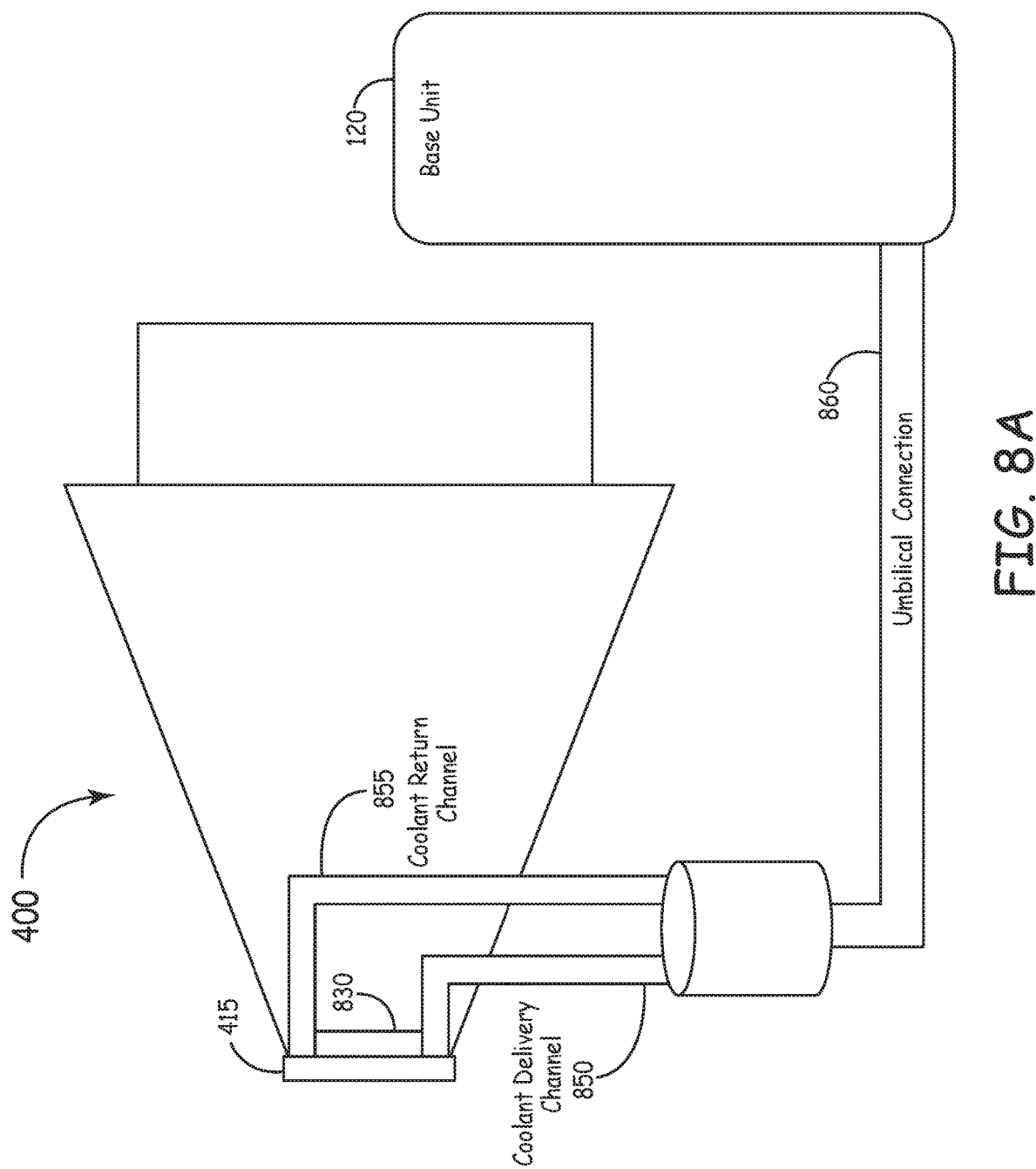

RECONFIGURABLE HANDHELD LASER TREATMENT SYSTEMS AND METHODS

RELATED APPLICATIONS

This application is a continuation application of U.S. application Ser. No. 14/736,300, filed Jun. 11, 2015, which is a continuation application of U.S. application Ser. No. 13/413,826, filed Mar. 7, 2012, now U.S. Pat. No. 9,149,332, granted on Oct. 6, 2015, which is a continuation-in-part application of U.S. application Ser. No. 13/363,570, filed Feb. 1, 2012, now U.S. Pat. No. 9,078,681, granted on Jul. 14, 2015. The complete disclosures of which are hereby incorporated by reference herein.

BACKGROUND

Hair removal is one example of a treatment performed by handheld laser treatment systems. Selective wavelengths of light from a laser source are absorbed by the melanin of a hair, which heats and kills a target hair follicle. Different fluence levels and applications techniques are appropriate for hair removal from different regions of the body. For example, there are regions of the body where precision application of a laser is needed, such the lip region, using devices that provide a concentrated high fluence beam applied to a relatively small area. For other regions, such as backs, chests or arms, less precision is needed. For these regions, devices and procedures can be used that treat larger areas, using relatively less fluence. However, for a physician, obtaining separate pieces of equipment for performing such treatments can be expensive.

For the reasons stated above and for other reasons stated below which will become apparent to those skilled in the art upon reading and understanding the specification, there is a need in the art for reconfigurable handheld laser treatment systems and methods.

SUMMARY

The Embodiments of the present invention provide for reconfigurable handheld laser treatment systems and methods and will be understood by reading and studying the following specification.

In one embodiment, a handheld laser treatment apparatus comprises: a handset including a treatment chamber, the treatment chamber having an open treatment aperture; a laser array arranged to project optical energy into the treatment chamber and coupled to a power source; at least one vacuum channel positioned within the treatment chamber and coupled to a vacuum source; a trigger sensor coupled to logic that controls activation of the laser array and the vacuum channel; an attachment sensor arranged to detect which of a plurality of attachments are inserted into the treatment chamber through the treatment aperture. The logic enables activation of the vacuum channel when the attachment sensor detects a first attachment of the plurality of attachments inserted into the treatment aperture. The logic disables activation of the vacuum channel when the attachment sensor detects a second attachment of the plurality of attachments inserted into the treatment aperture.

DRAWINGS

Embodiments of the present invention can be more easily understood and further advantages and uses thereof more readily apparent, when considered in view of the description of the preferred embodiments and the following figures in which:

FIGS. 4, 4A and 4B are diagrams illustrating an optical condenser adapter of one embodiment of the present invention for use with a reconfigurable handset;

FIGS. 5, 5A and 5B are diagrams illustrating various means for identifying a present reconfigurable handset configuration;

FIGS. 8, 8A, 9, 9A and 10 are each diagrams illustrating alternate cooling mechanism embodiments for optical condenser adapter attachment for a reconfigurable handset.

In accordance with common practice, the various described features are not drawn to scale but are drawn to emphasize features relevant to the present invention. Reference characters denote like elements throughout figures and text.

DETAILED DESCRIPTION

Figure 1:
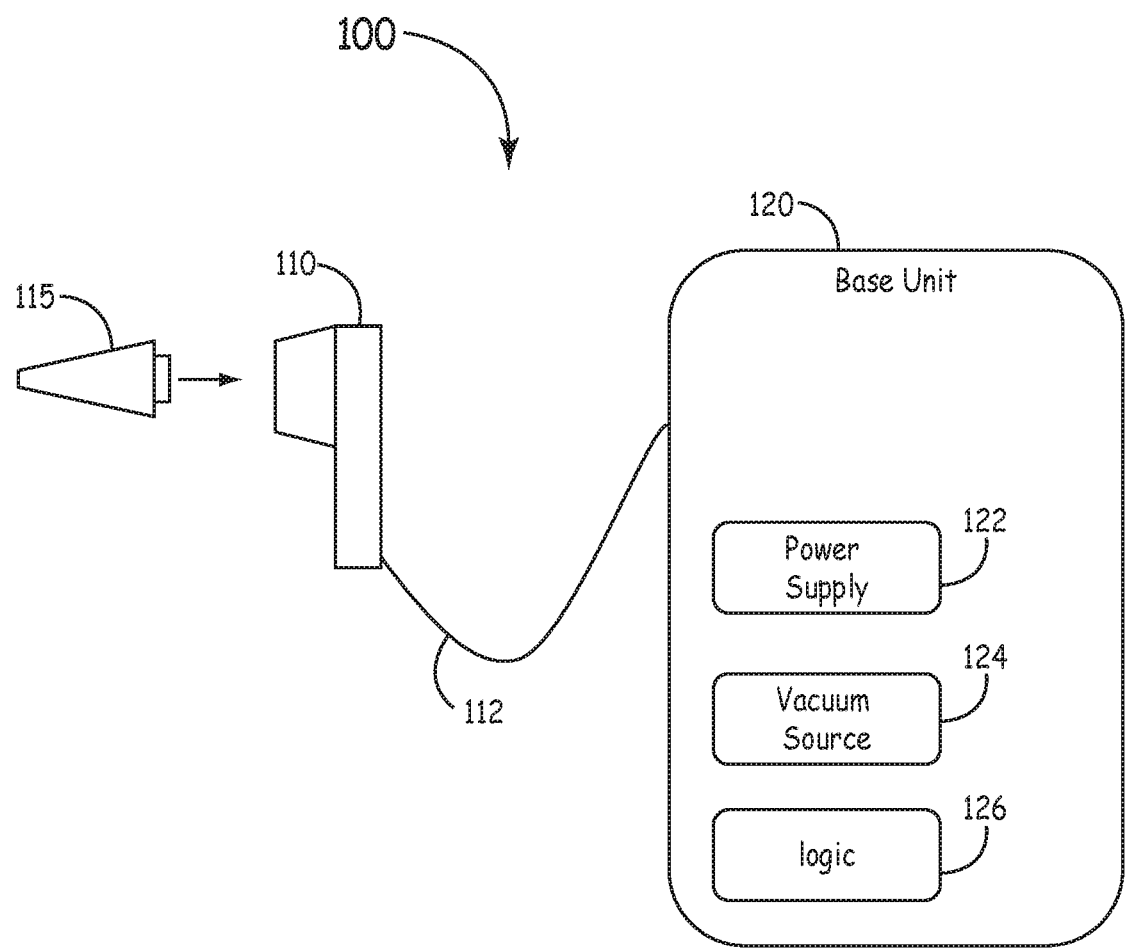
FIG. 1 is a diagram of a laser treatment system of one embodiment of the present invention.

In the following detailed description, reference is made to the accompanying drawings that form a part hereof, and in which is shown by way of specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

Embodiments of the present invention provide for laser treatment systems and methods utilizing a single handset that is adaptable in configuration for different treatment procedures, thus eliminating the need for multiple handsets. For example, in one embodiment a handset may be configured to perform a high optical fluence treatment to a small treatment area. In another configuration the high fluence treatment is performed through a contact element which in addition to its optical characteristics it also cools the tissue in order to protect its surface and to allow a safe delivery of the higher fluences deep into a target tissue. In another configuration, the same handset may be configured to provide a wide area low optical fluence vacuum assisted laser treatment. This is accomplished through the use of a plurality of attachments, such as a hygienic insert or an optical condenser adapter, which may be installed within, or removed from, the laser handset.

As mentioned above, in one configuration of one embodiment, the handset provides a treatment chamber that may be used for performing vacuum assisted laser treatments. A laser array within the handset delivers optical energy into the treatment chamber. In this embodiment when the handset is used in this configuration, a region of the patient's skin seals a treatment aperture of the treatment chamber while a vacuum is applied by the handset to pull/suck in at least a portion of the skin towards the laser array. When the requisite vacuum level is detected within the chamber, the laser array is activated to release a laser pulse.

In another configuration of this embodiment with an optical condenser adapter installed, the handset provides for treatment to a more localized region of the skin, applying higher fluence to the region under treatment than the vacuum assisted laser treatment. The optical condenser adapter redirects optical energy from the handset laser array to concentrate the optical energy to an output aperture at the adapter's tip that provides a much smaller treatment area as compared to the treatment chamber of the handset. For example, in one embodiment, the aperture at the adapter's tip is a 9×9 mm square as opposed to a 22×35 mm treatment aperture of the handset.

Also, as explained in greater detail below, in some embodiments the tip of the optical condenser adapter includes a cooling mechanism, such as a cooled crystal. Cooling the skin is desirable for many applications when using the optical condenser adapter because of the relatively high fluence of the laser pulse applied to the skin. For example, in one embodiment, a handset with the optical condenser adapter installed may release up to approximately 100 J/cm$^2$. The cooled crystal cools the surface of the skin so that energy absorbed goes down to the target hair follicle (or other target tissues) and is not significantly absorbed by upper levels of the skin. Cooling provides a safety feature that reduces the risks of burns to the upper levels of the skin while still permitting heating of target tissues below. In comparison, the vacuum assisted laser treatments can utilize a much lower fluence, on the order of 12 J/cm$^2$, because the stretching of the skin pulls target tissues closer to the skin surface, requiring less penetration.

FIG. 1 is a diagram of a laser treatment system 100 of one embodiment of the present invention. Laser treatment system 100 includes a reconfigurable handset 110 coupled to a base unit 120 by a cable 112. As will be described in greater detail below, system 100 may further includes=an optical condenser adapter 115 which may operate as an attachment to handset 110. Without optical condenser adapter 115, handset 110 is operable to perform treatments such as the vacuum assisted laser treatments as discussed above. Such applications may generally be considered non-contact applications, although in some circumstances where there is more available tissue, the chucked tissue may come in contact with the back of the hygienic insert installed within the handset 110. When optical condenser adapter 115 is coupled to handset 110, the handset 110 is converted from a large-area low-fluence instrument into a relatively small-area high-fluence instrument. Such applications may generally be considered non-contact applications because an optical element of the optical condenser adapter 115 is typically placed in contact with a treatment area. For this reason, cooling elements may be incorporated into optical condenser adapter 115 as discussed below. In one embodiment, the base unit 120 comprises at least one power supply 122, a vacuum source 124, and logic 126 that support the treatment functions provided by reconfigurable handset 110 as described herein.

Figure 2:
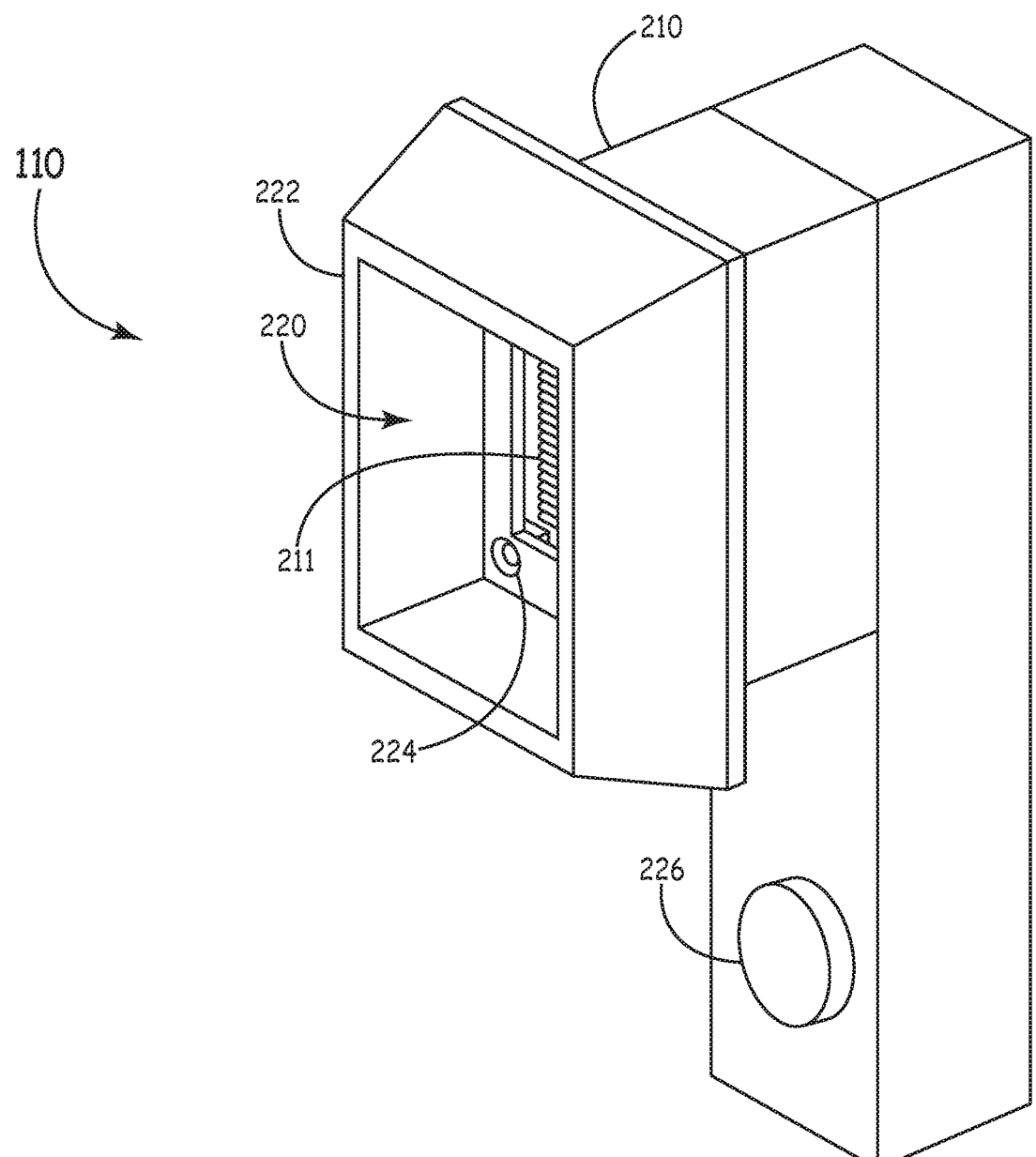
FIG. 2 is a diagram illustrating one embodiment of reconfigurable handset.

FIG. 2 is a diagram illustrating one embodiment of reconfigurable handset 110. Optical energy is generated by handset 110 using a laser source 210, which in one embodiment comprises a laser array 211. A treatment chamber 220 is positioned within handset 110, which defines a space to which optical energy from laser source 210 is provided. Treatment chamber 220 includes a treatment aperture 222. In one embodiment, treatment aperture 222 serves as an interface between handset 110 and a hygienic insert as described below. In other embodiments, treatment aperture 222 provides an interface that accepts an optical condenser adapter 115, as described below. Treatment chamber 220 further includes at least one vacuum channel 224 through which a vacuum is pulled to draw patient skin tissue under treatment into the treatment chamber 220. In one embodiment, vacuum channel 224 is coupled to the vacuum source 124 of base unit 120 via cable 115. In one embodiment, vacuum source 124 comprises a vacuum pump. In other embodiments, vacuum source 124 regulates a vacuum provided by an external source. Activation of both the laser source 210 and vacuum channel 224 are initiated by a trigger 226.

Figure 3:
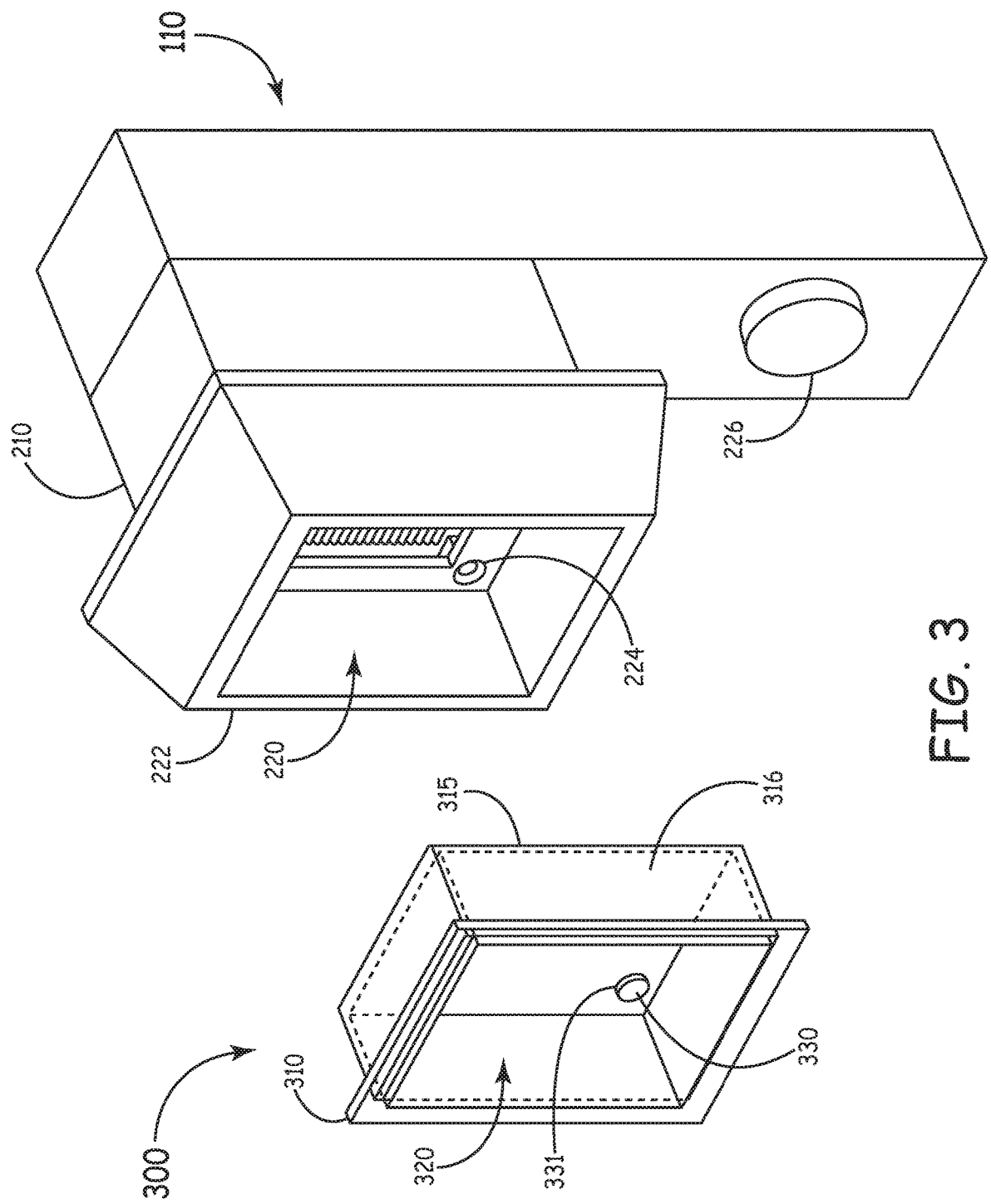
FIGS. 3 and 3A are diagrams illustrating a hygienic insert of one embodiment of the present invention.
Figure 3A:
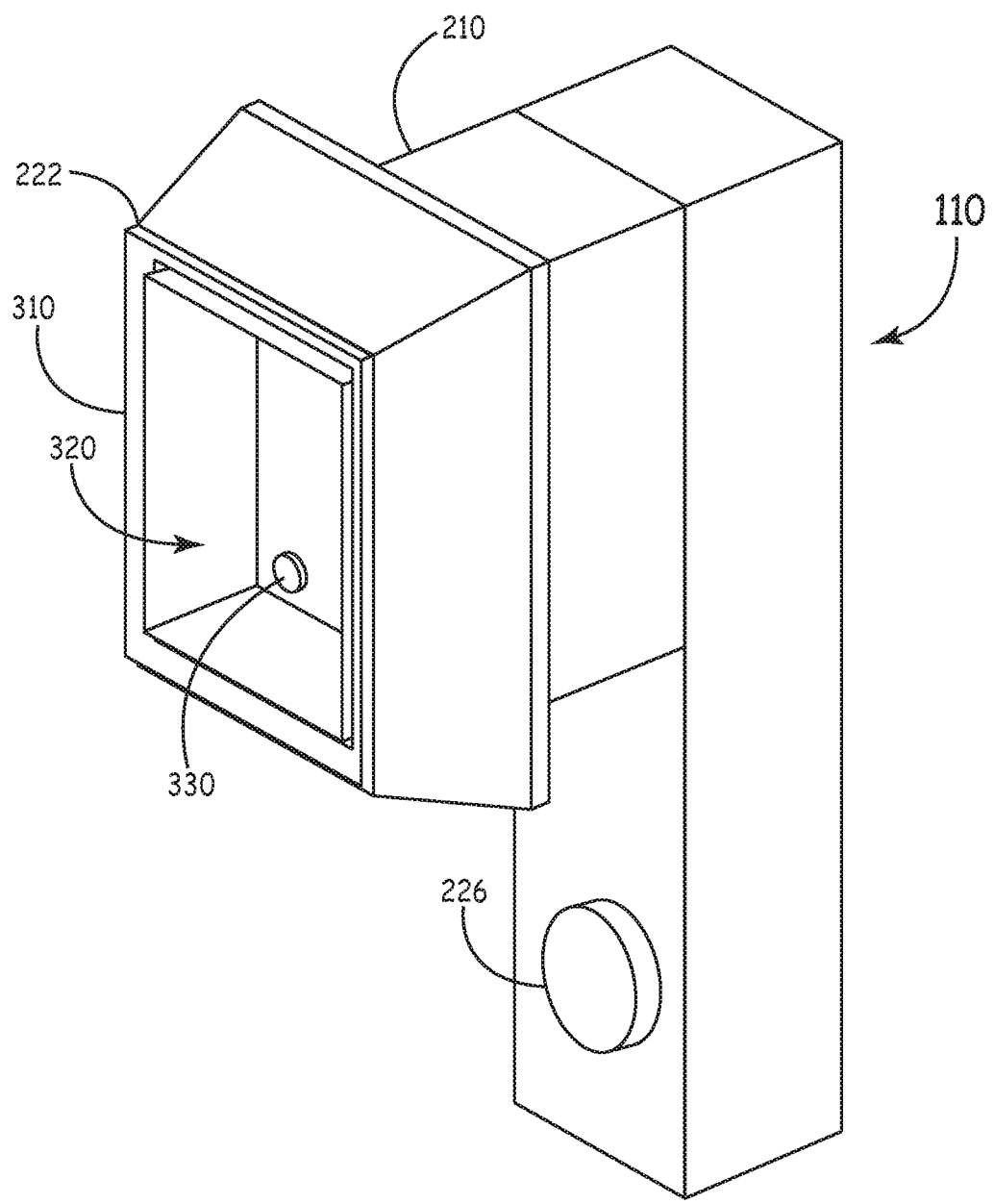

FIGS. 3 and 3A are diagrams illustrating a hygienic insert 300 of one embodiment of the present invention. Hygienic insert 300 comprises a base 315 at least partially comprising a material transparent to at least a portion of the spectrum emitted by laser source 210. Hygienic insert 300 further comprises an outer wall 316 extending from the base 315 to form a cavity 320 within the Hygienic insert 300. Base 315 and outer wall 316 define that portion of Hygienic insert 300 which is inserted into treatment chamber 220 of handset 110. As such, base 315 and outer wall 316 together have a size and shape compatible with insertion into treatment chamber 220 of handset 110. Hygienic insert 300 further comprises a peripheral flange 310 around a periphery of outer wall 316. Peripheral flange 310 provides the interface between handset 110 and patient skin tissue under treatment. As illustrated in FIG. 3, hygienic insert 300 also includes at least one channel 330 which communicates the negative air pressure pulled via vacuum channel 224 with cavity 320. In one embodiment, channel 330 aligns with the vacuum channel 224 of handset 110 to form a surface seal. In other embodiments, channel 330 at least partially inserts into vacuum channel 224. In still other embodiments, vacuum channel 224 at least partially penetrates into cavity 320 through an opening provided by channel 330. FIG. 3A illustrates a hygienic insert 300 completely inserted into handset 110.

In one embodiment, in operation, when the handset 110 is placed onto a region of patient skin tissue, the skin seals against flange 310. Then, when the operator activates trigger 226, a vacuum is applied within cavity 320 by vacuum channel 224 which sucks in at least a portion of the patient skin tissue into the volume within treatment chamber 220 and towards the laser source 210. When a requisite vacuum level is detected within the chamber 220 (such as described in further detail below), the laser source 210 releases at least one laser pulse.

The treatment procedure applied to the patient skin tissue can result in tissue debris accumulating within the cavity 320 of hygienic insert 300. Since the purpose of hygienic insert 300 is to contain and limit contamination, in one embodiment, hygienic insert 300 includes an integrated particle filter 331 within channel 330 to prevent tissue debris from being pulled into vacuum channel 224, vacuum source 125 and/or any other upstream equipment.

Figure 4A:
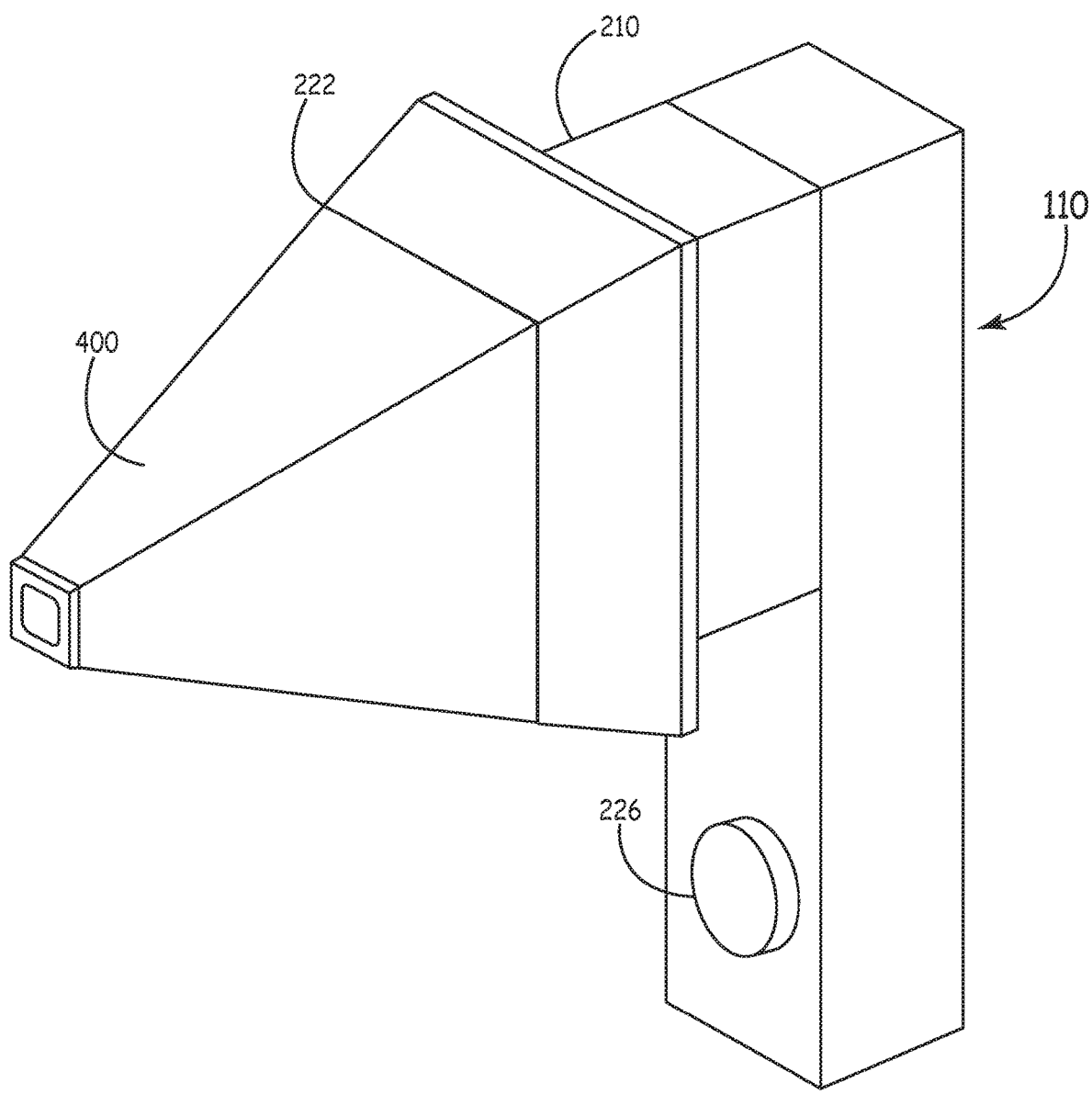
Figure 4B:
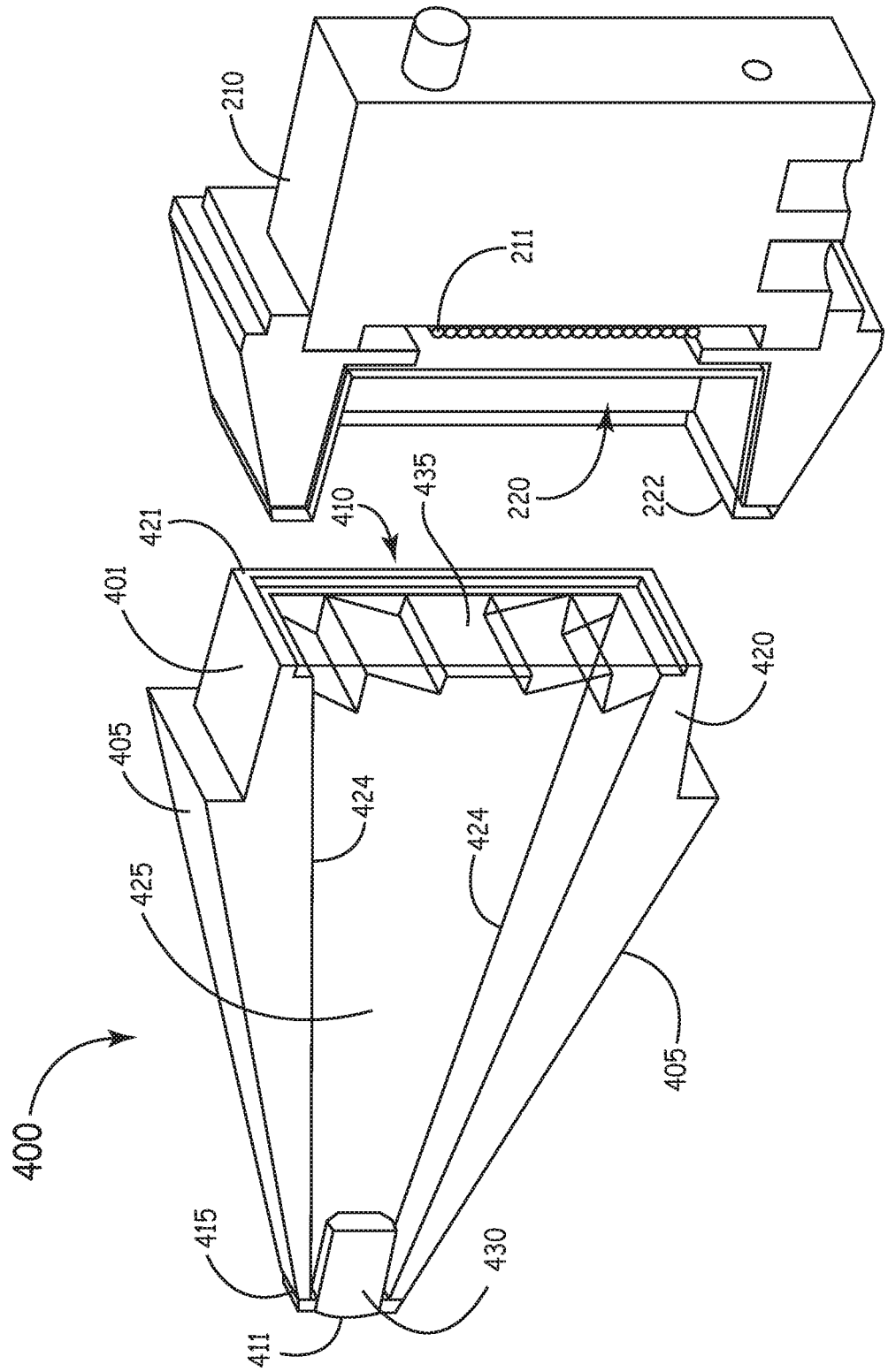

FIGS. 4, 4A and 4B are diagrams illustrating an optical condenser adapter 400 of one embodiment of the present invention such as optical condenser adapter 115 for use with reconfigurable handset 110. Embodiments of optical condenser adapter 400 permit an operator to quickly and easily reconfigure handset 110 for a different treatment procedure by swapping hygienic insert 300 for optical condenser adapter 400, and vise verse. Optical condenser adapter 400 functions by condensing the optical power of light received through a relatively large aperture from laser source 210 for emission from a relatively smaller aperture. In doing so, the density of the optical energy provided by system 100 (referred to herein as fluence) is increased.

In one embodiment, optical condenser adapter 400 comprises handset adapter interface 401. Similar to hygienic insert 300, handset adapter interface 401 has a size and shape compatible with insertion into treatment chamber 220 of handset 110 as shown in FIG. 4A. In one embodiment, handset adapter interface 401 includes a base 421 and outer wall 420.

Optical condenser adapter 400 includes at least two optical members. A first optical member 435 is located within the base 421 of handset adapter interface 401. The first optical member 435 provides an input aperture 410 that receives the parallel beams of laser light from laser source 210 and shifts the path of the optical energy from the laser light towards the center of optical condenser adapter 400. More particularly, the path of the optical energy is shifted by the configuration of first optical member 435 so that the laser light received by first optical member 435 via aperture 410 is concentrated onto a second optical member 430 located at an output aperture 411 of optical condenser adapter 400. The second optical member 430, in turn, again shifts the path of the optical energy so that the beams of laser light exiting from aperture 410 are once again aligned. In one embodiment, the internal region 425 of optical condenser adapter 400 between the first optical member 435 and the second optical member 430 is an open volume. A cooling element 415 (further discussed below) is provided at output aperture 411 for removing heat absorbed by surface tissues during treatment of deeper tissues. In one embodiment, cooling element 415 may be a cooling crystal. In another embodiment, instead of being separate elements, the cooling element 415 and the second optical element 430 are the same.

In one embodiment, one or both of the first optical member 435 and the second optical member 430 are Fresnel lenses. For example, in the embodiment illustrated in FIG. 4B, first optical member 435 is a Fresnel lens comprising five crystal regions, each receiving a different subset of parallel laser light from different elements of laser array 211. Each of the five crystal regions has a different Fresnel lens angle to concentrate the optical energy it receives towards the center of optical condenser adapter 400 and second optical member 430. The angles used for each crystal region are readily determined by one of ordinary skill in the art, after reading this specification, by taking into consideration the geometry of optical condenser adapter 400, including the dimensions of apertures 410 and 411 and the distance between the first optical member 435 and the second optical member 430. In one embodiment, second optical member 430 includes a Fresnel lens having crystal regions angled to correspond to angles of each received subset received from first optical member 435.

As would be appreciated by one of ordinary skill in the art, embodiments of the present invention are not limited to those utilizing Fresnel lenses and in other embodiments other optical elements may be used. Further, multiple and different implementations of optical condenser adapter 400 can be realized to provide the operating physician with different size and shape configurations for output aperture 411. For example, for different implementations, output aperture may be round, elliptical, diamond, square, or any other geometric shape or combination of shapes. In still other implementations, an optical condenser adapter 400 may be tuned for use with specific wavelengths of light emitted from laser source 210, such as through the selection of particular materials for one or both of the first optical member 435 and the second optical member 430. In one embodiment of the condenser adapter 400 the inner surfaces of outer walls 405 that face internal region 425 are coated with reflective material which reduces optical energy loss during light propagation from the first optical element 435 to the second optical element 430.

Figure 5:
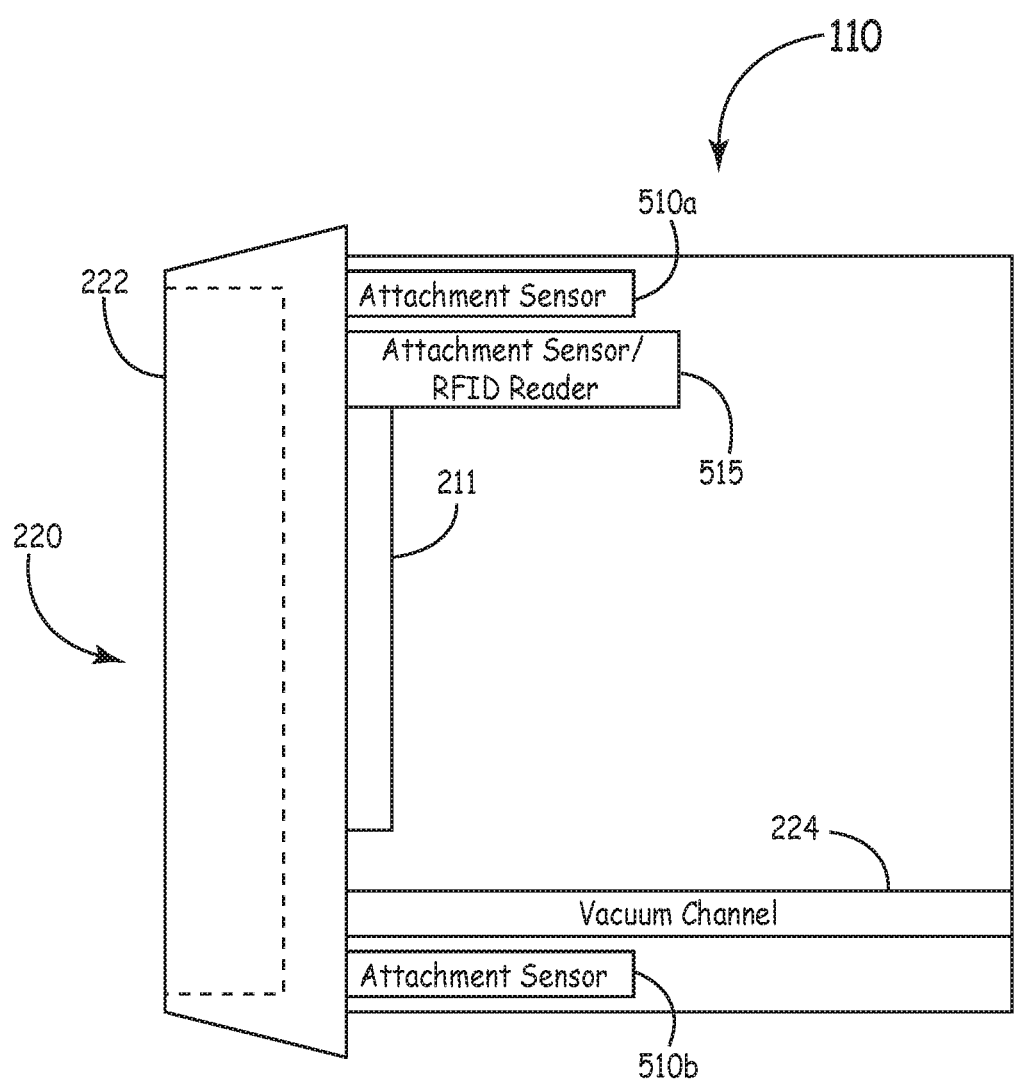
Figure 5A:
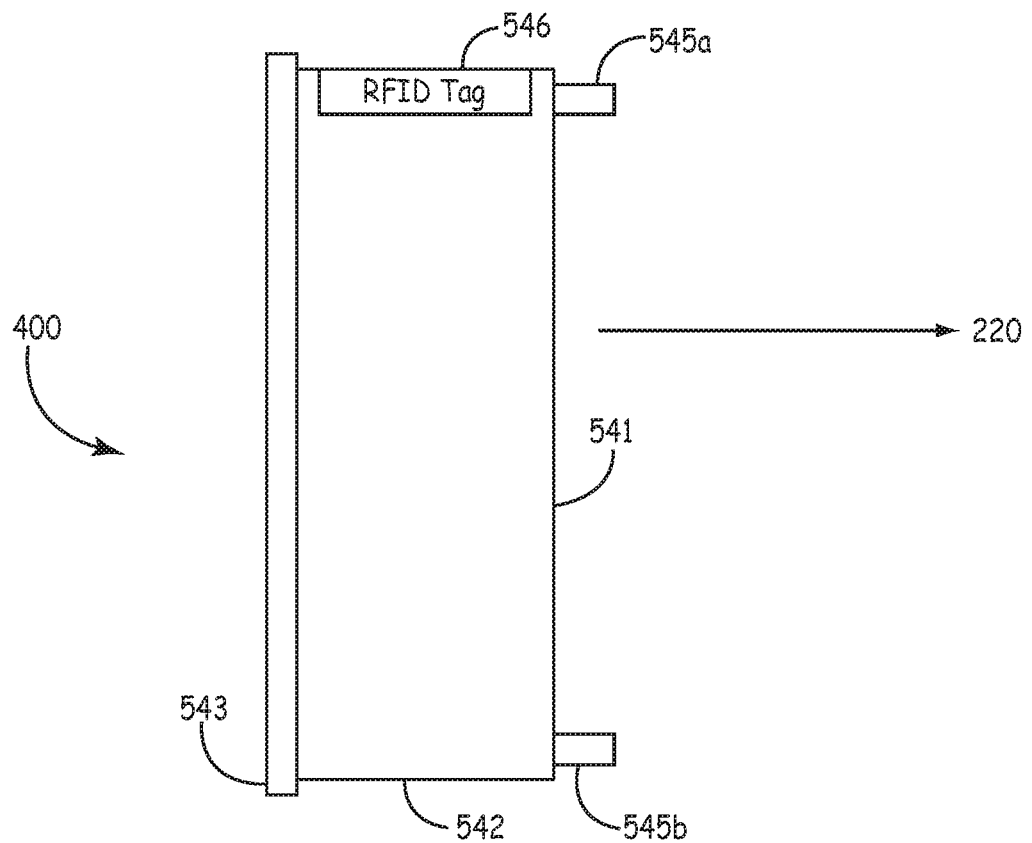

FIGS. 5, 5A and 5B are diagrams illustrating various means for identifying the present configuration of handset 110. For example, FIG. 5 illustrates one or more alternate embodiments of handset 110 having one or more attachment sensors such as 510a, 510b and 515.

In one embodiment, handset 110 comprises one or more attachment sensors 510a, 510b, which identify what attachment, if any, is inserted into chamber 220. For example, one alternate implementation of hygienic insert 300 (shown in FIG. 5A) optionally further comprises one or both of pins 545a and 545b. Similarly, one implementation of optical condenser adapter 400 (shown in FIG. 5B) optionally further comprises one or both of pins 565a and 565b. In one embodiment, attachment sensors 510a, 510b detect the which set of pins (i.e., 545a/545b or 565a/565b) are present and associates the particular pattern of present pins to identify which attachment is inserted into chamber 220. Upon insertion of either hygienic insert 300 or optical condenser adapter 400, differing patterns of pins may be identified, for example, based on pin locations, numbers of pins, pin lengths, or electrical properties. An absence of detected pins may indicate that nothing is inserted.

In another embodiment, handset 110 comprises attachment sensor 515 which includes an RFID reader 515. For example, one alternate implementation of hygienic insert 300 (shown in FIG. 5A) optionally comprises an RFID tag 546. Similarly, one implementation of optical condenser adapter 400 (shown in FIG. 5B) optionally comprises an RFID tag 566. In one embodiment, attachment sensor 515 reads attachment data from the RFID tag of the attachment inserted into chamber 220 (i.e., 546 or 566) to identify which attachment is inserted into chamber 220. In one embodiment, an absence of a detected RFID tag may indicate that nothing is inserted.

In some implementations of optical condenser adapter 400, the attachment data from the RFID tag 566 can indicate the particular configuration of optical condenser adapter 400, such as the size and/or shape of output aperture 411 and whether that particular adapter is tuned for a particular wavelength. In one embodiment, system 100 verifies the attachment data from the RFID tag 566 is appropriate for the currently selected treatment parameters. For example, if the attachment data indicates that optical condenser adapter 400 is only to be used for specific wavelength, and laser source 210 is configured to emit a different wavelength, system 100 may provide the operator with a warning and/or prohibit firing of laser source 210.

In some implementations, RFID reader 515 can further write information onto an RFID tag of an attachment. For example, in one implementation RFID reader 515 writes data onto an RFID tag 546 of an hygienic insert 300 indicating when the hygienic insert 300 has been used. If an operator inadvertently installs a previously used hygienic insert 300, system 100 may provide the operator with a warning and/or prohibit operation of laser source 210. In one embodiment, a unique session ID is written onto RFID tag 546 to permit reuse of a hygienic insert 300 on the same patient during a particular treatment session but otherwise prevent its reuse. Similarly, data may optionally also be written onto RFID tag 566 of optical condenser adapter 400.

Figure 6:
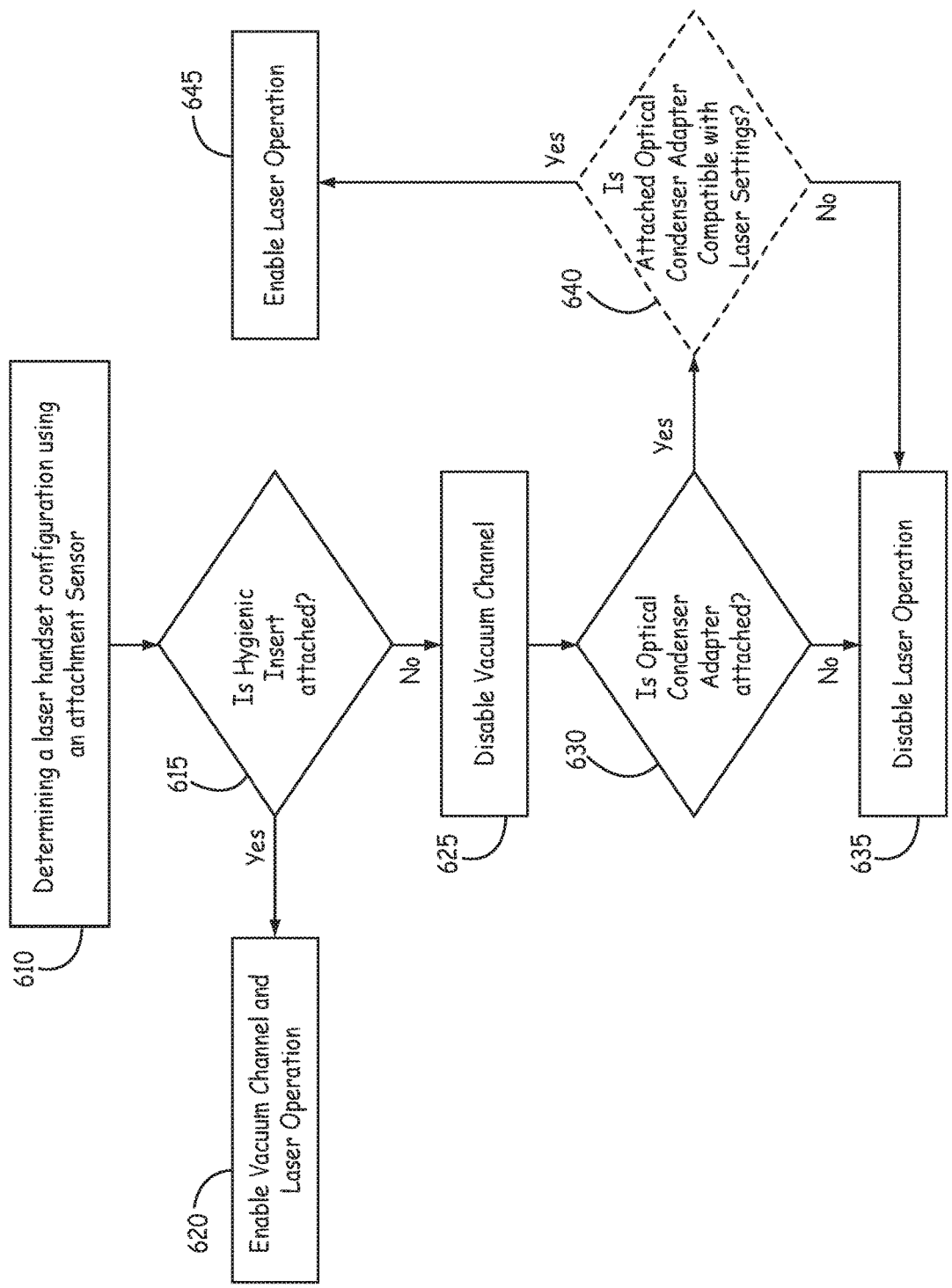
FIG. 6 is a flow chart illustrating a method of one embodiment of the present invention relating to detecting and controlling the operation of a laser treatment system based on the detected configuration of a reconfigurable handset.

FIG. 6 is a flow chart illustrating a method of one embodiment of the present invention relating to detecting and controlling the operation of laser system 100 based on the detected configuration of handset 110. The method starts at 610 with determining a laser handset configuration using an attachment sensor. In some embodiments, the attachment sensor may determine the configuration using pin configurations and/or RFID tags, such as described above with respect to FIG. 5. In other embodiments, other detection means may be used. The method proceeds to 615 with determining whether a hygienic insert is attached to the laser handset. When a hygienic insert is attached, the method proceeds to 620 with enabling operation of a vacuum channel and laser source. That is, with a hygienic insert, such as insert 300, installed in handset 110, the handset is configured for vacuum assisted laser treatments such as described above. In this configuration, when the laser handset is placed onto a region of patient skin tissue, the skin seals against a flange of the hygienic insert. Then, when the operator activates a trigger, a vacuum is applied within a cavity of the insert by a vacuum channel in the handset. The vacuum sucks in at least a portion of the patient skin tissue into the cavity and towards the laser source of the handset.

When a hygienic insert is not attached (determined at 615), the method proceeds to 625 with disabling the vacuum channel of the handset. Disabling the vacuum channel of the handset when no hygienic insert is detected prevents inadvertent non-hygienic use of the handset for vacuum assisted laser treatments. If no hygienic insert is detected because an optical condenser adapter is instead installed, then operation of the vacuum channel is unnecessary and may be disabled to prevent wear.

The method next proceeds to 630 with determining whether an optical condenser adapter is attached to the laser handset. In the case where no optical condenser adapter is detected, and no hygienic insert is detected, then the laser handset may not be properly set up for use and the method proceeds to 635 with disabling laser operation. In one embodiment, when it is determine that an optical condenser adapter is attached, the method proceeds to 645 with enabling laser operation. In one embodiment, the method optionally proceeds to 640 with determining whether the attached optical condenser adapter is compatible with the present laser settings. If not, the method proceeds to 635 with disabling laser operation. When the adapter and present laser setting are compatible, the method proceeds to 645 with enabling laser operation.

Figure 7:
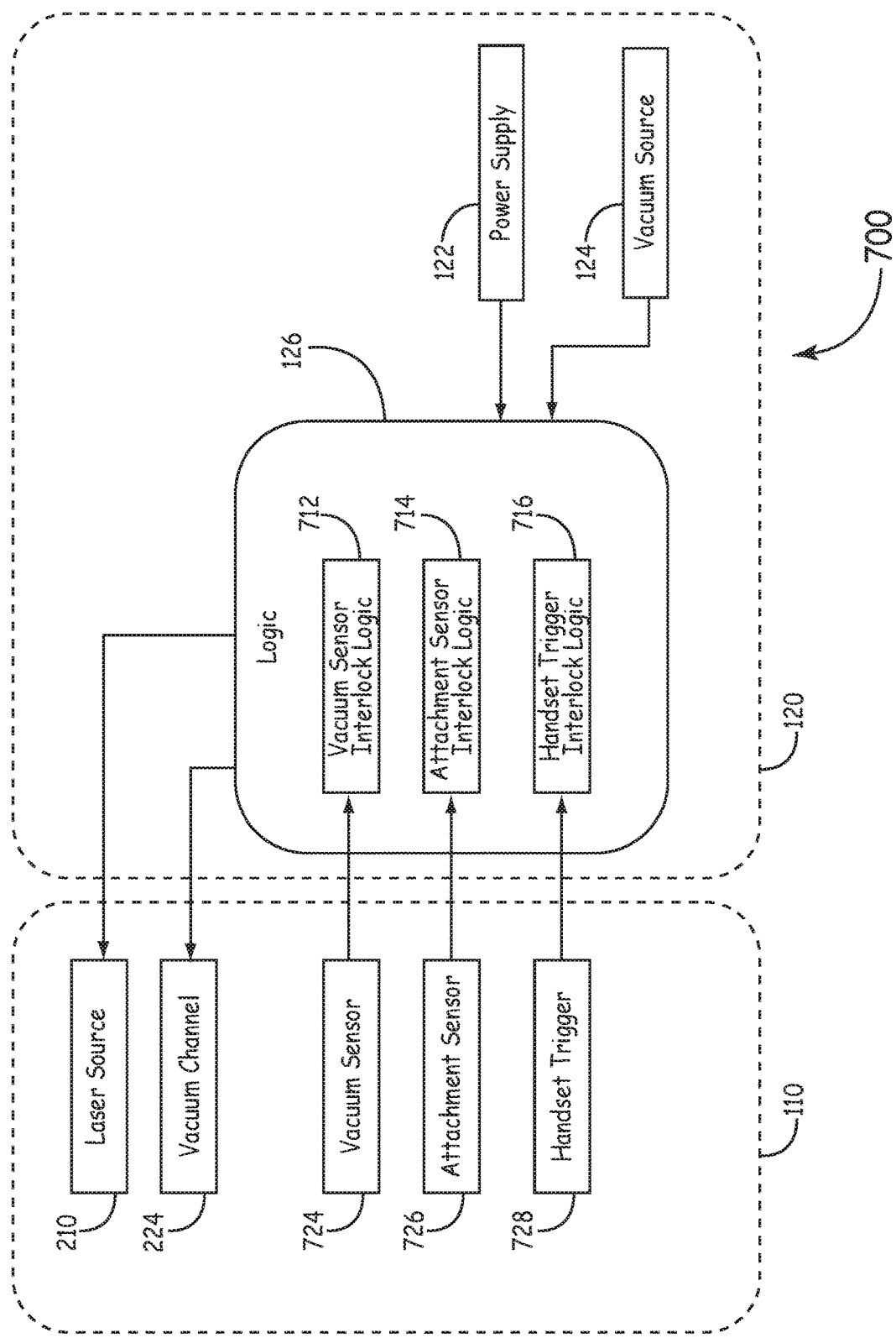
FIG. 7 is a block diagram illustrating one embodiment of a configuration of a laser treatment system.

FIG. 7 is a block diagram illustrating at 700 one embodiment of a configuration of system 100 for implementing the method described in FIG. 6. Handset 110 comprises laser source 210, vacuum channel 224, a vacuum sensor 724, an attachment sensor 726 (such as attachment sensors 510a,b and 515, for example) and trigger sensor 728. As illustrated above, base unit 120 comprises power supply 122, vacuum source 126 and logic 126. Power supply 122 provides the electrical energy for operating laser source 210. Vacuum source 740 provides the negative pressure for operating vacuum channel 224. In this embodiment, logic 126 comprises one or more interlocks (712, 714, 716) for controlling operation of laser source 210 and vacuum channel 224 based on inputs received from vacuum sensor 724, attachment sensor 726, and trigger sensor 728.

For example, in one embodiment, attachment sensor interlock logic 714 receives inputs representing the state of attachment sensor 726. When a hygienic insert 300 is detected by attachment sensor 726, attachment sensor interlock logic 714 enables operation of vacuum channel 224. Otherwise, when an optical condenser attachment is detected, operation of vacuum channel 224 is disabled by attachment sensor interlock logic 714. In alternate embodiments, enabling or disabling of vacuum channel 224 may be achieved, for example, by altering a valve alignment between vacuum source 124 and vacuum channel 224 or by electrically controlling vacuum source 740. Attachment sensor interlock logic 714 may disable operation of both vacuum channel 224 and laser source 210 when no attachment is detected. Similarly, attachment sensor interlock logic 714 may disable operation of both of vacuum channel 224 and laser source 210 when it detects an incompatibility between the attachment and the present laser settings or other system parameters.

Trigger sensor interlock logic 716 receives inputs representing the state of trigger sensor 728. In one embodiment, when trigger sensor 728 is depressed, that indicates to logic 710 that the operator wants to activate the laser source 210.

Assuming that a hygienic insert 300 is attached and laser and vacuum operation have not been disabled by attachment sensor interlock logic 714, trigger sensor interlock logic 716 will activate vacuum channel 224. Vacuum sensor 724 monitors vacuum within cavity 320 and is coupled to vacuum sensor interlock logic 712. In one embodiment, as long as vacuum sensor interlock logic 712 determines that the vacuum within cavity 320 is insufficient (i.e., not meeting a predetermined pressure threshold), it blocks operation of laser source 210. When vacuum sensor interlock logic 712 determine that there is a sufficient vacuum within cavity 320, it proceeds with firing of laser source 210.

Assuming that an optical condenser adapter 400 is attached, laser operation should not be disabled by attachment sensor interlock logic 714, while vacuum operation will be disabled by attachment sensor interlock logic 714. In that case, vacuum sensor interlock logic 712 is bypassed and trigger sensor interlock logic 716 will activate laser source 210 directly based on the state of trigger sensor 720.

FIGS. 8, 8A, 9, 9A and 10 are diagrams illustrating alternate cooling mechanism embodiments for optical condenser adapter 400. As mentioned above, optical condenser adapter 400 comprises a cooling element 415 at output aperture 411 which functions to cool upper layers of skin while the optical energy emitted by output aperture 411 treats tissues located at lower layers beneath the skin's surface. In order to perform this function, heat absorbed by cooling element 415 must be removed so that cooling element 415 continues to have a sufficient heat absorbing capacity.

Figure 8:
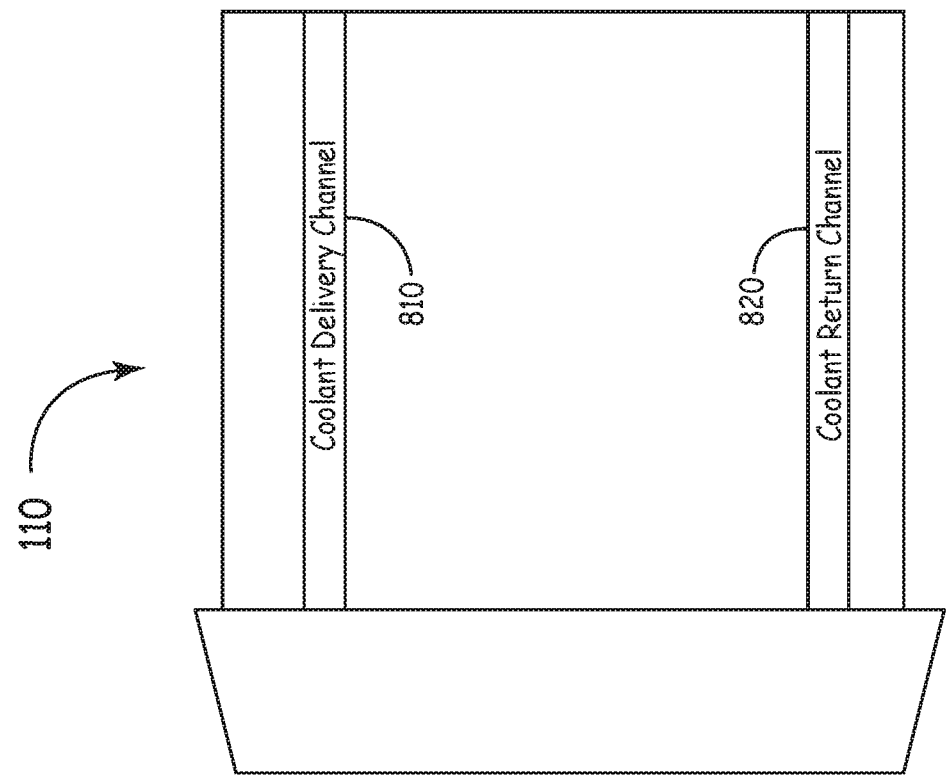
Figure 8:
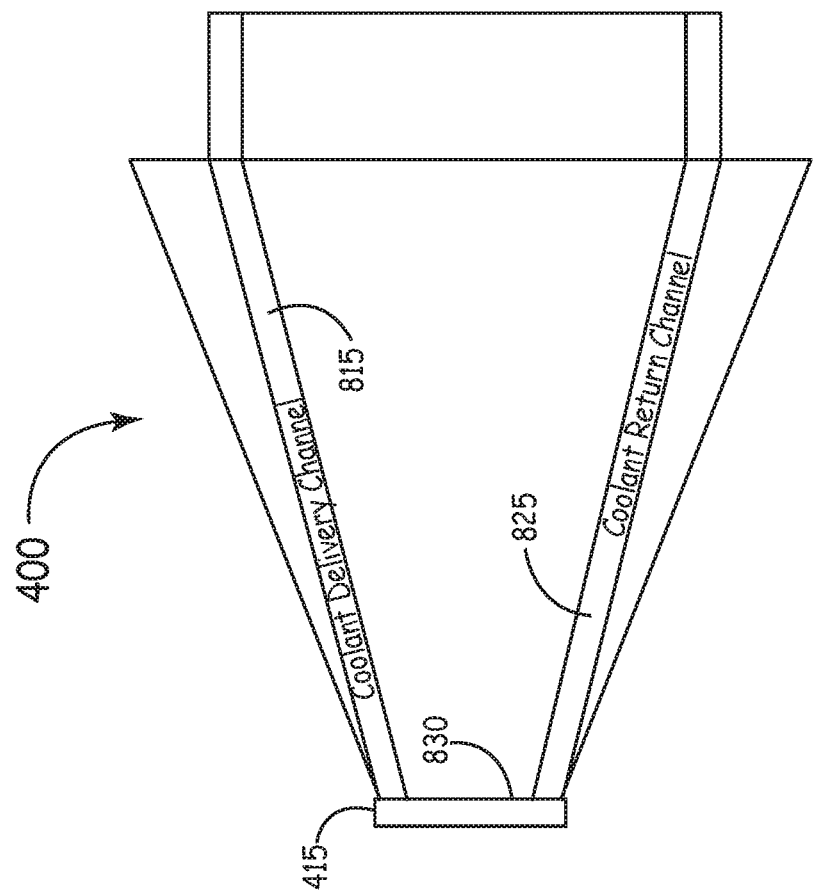

In the embodiments illustrated in FIGS. 8 and 8A, heat is removed from cooling element 415 by a pre-cooled circulating liquid coolant. In FIG. 8, handset 110 further comprises a coolant delivery channel 810 and a coolant return channel 820. In this embodiment, optical condenser adapter 400 further comprises a coolant delivery channel 815, a heat exchanging interface 830 interfacing with cooling element 830, and a coolant return channel 825. With optical condenser adapter 400 coupled to handset 110, channels 810 and 820 are coupled to respective channels 815 and 825 to form a complete circulating coolant circuit. In operation, pre-cooled circulating liquid coolant is provided by handset 110 by channel 810 to heat exchanging interface 830 via channel 815. At heat exchanging interface 830, the pre-cooled circulating liquid coolant absorbs the thermal energy accumulating in cooling element 415 and removes that heat through channels 825 and 820.

An alternate but similar embodiment is illustrated in FIG. 8A. Instead of having pre-cooled circulating liquid coolant delivered by handset 110, coolant delivery channel 850 and coolant return channel 855 in optical condenser adapter 400 are coupled via an umbilical connection 860 to base unit 120. In this embodiment, in operation, pre-cooled circulating liquid coolant is provided to coolant delivery channel 850 by umbilical connection 860. At heat exchanging interface 830, the pre-cooled circulating liquid coolant absorbs the thermal energy accumulating in cooling element 415 and removes that heat through coolant return channel 855 back through umbilical connection 860 to base unit 120.

Figure 9:
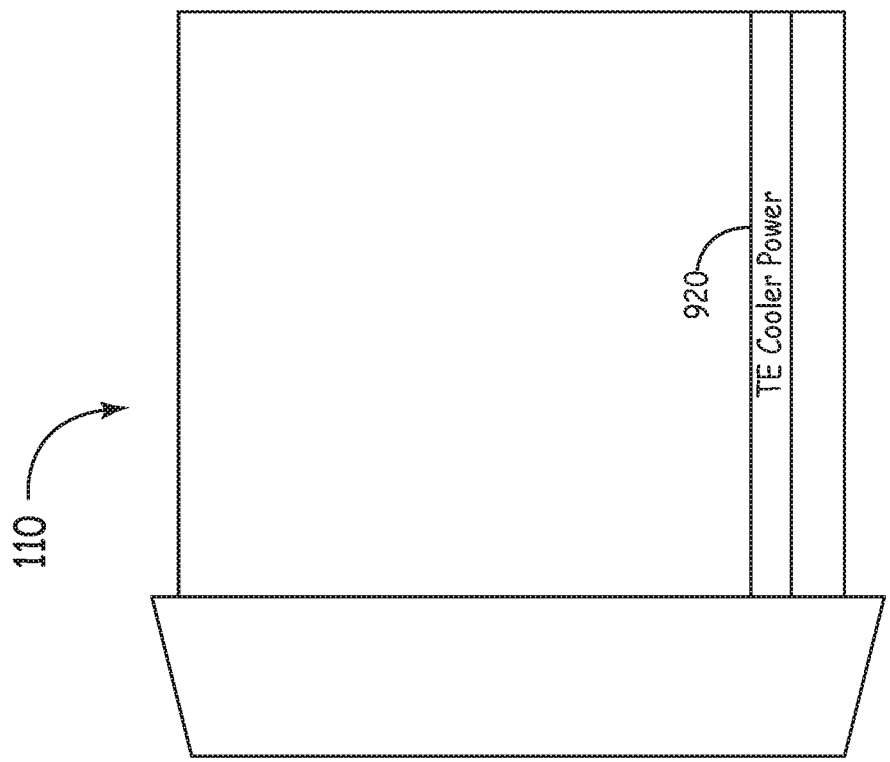
Figure 9:
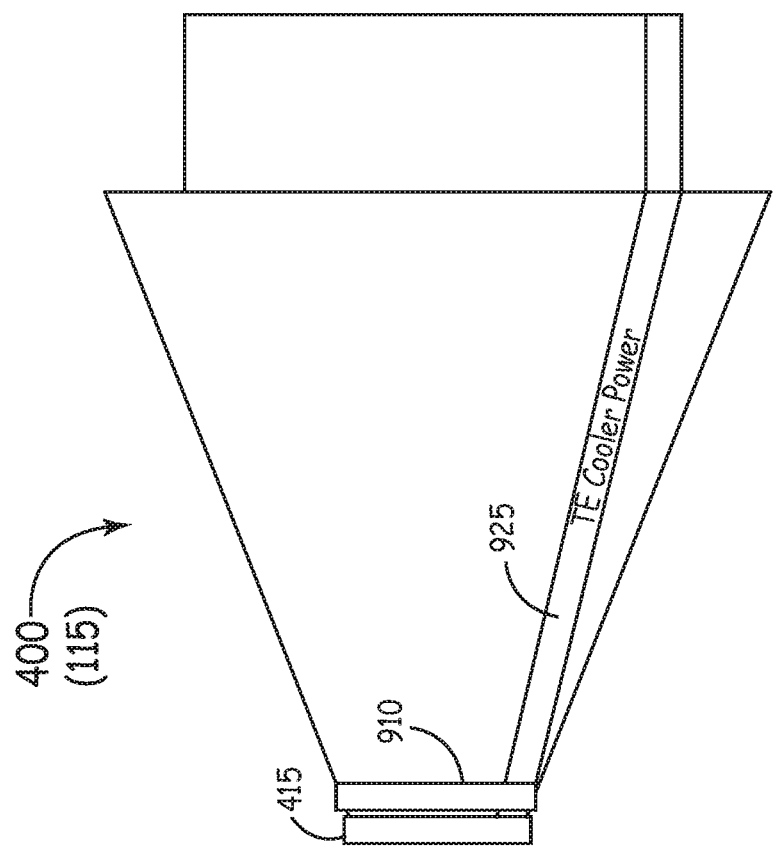
Figure 9A:
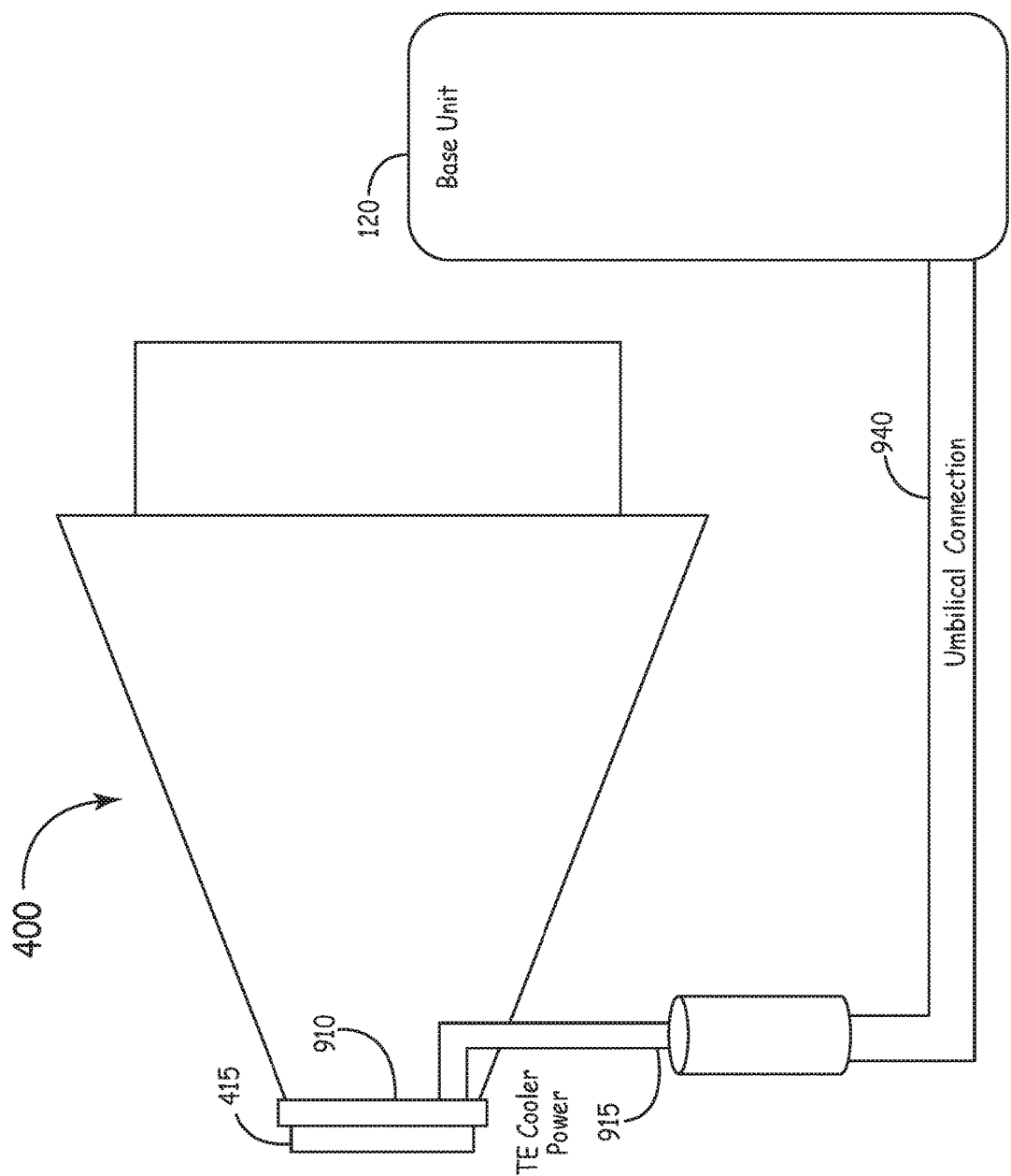

In the embodiments illustrated in FIGS. 9 and 9A, heat is removed from cooling element 415 by a thermoelectric cooling device 910 coupled to crystal 415.

In FIG. 9, handset 110 further comprises cooler power conductors 920. A corresponding set of cooler power conductors 925 are integrated into optical condenser adapter 400. Cooler power conductors 925 in turn are electrically coupled to thermoelectric cooling device 910. With optical condenser adapter 400 coupled to handset 110, cooler power conductors 920 are coupled to respective Cooler power conductors 925 to form an electrical circuit powering thermoelectric cooling device 910. In operation, electrical power is provided by handset 110 to thermoelectric cooling device 910 which absorbs the thermal energy accumulating in cooling element 415 and dissipates the heat away from cooling element 415. An alternate embodiment is illustrated in FIG. 9A. Instead of having electric power for thermoelectric cooling device 910 delivered by handset 110, Cooler power conductors 915 in optical condenser adapter 400 instead receive electrical power from base unit 120 via an umbilical connection 940 to base unit 120.

Figure 10:
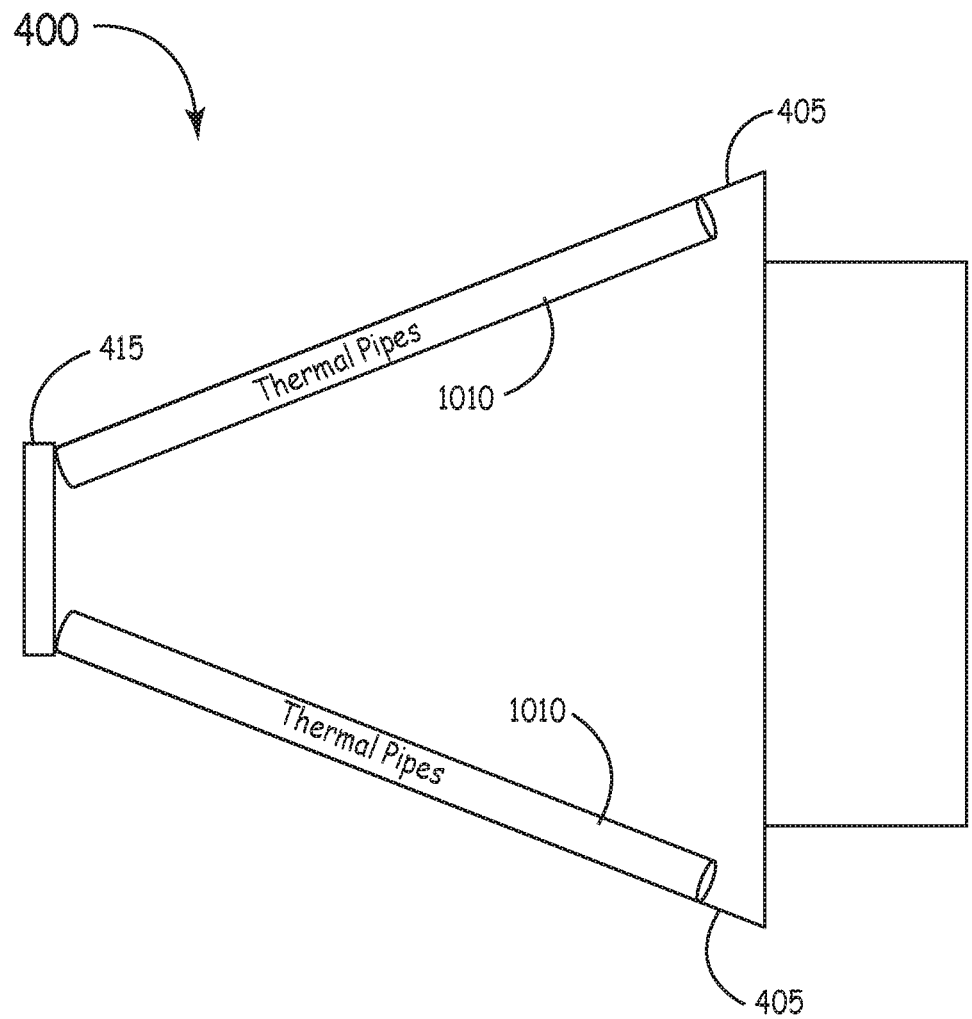

In the embodiments illustrated in FIG. 10, heat is removed from cooling element 415 by thermal pipes 1010 integrated into optical condenser adapter 400. In operation, thermal pipes 1010 absorb the thermal energy accumulating in cooling element 415 and dissipates the heat away from cooling element 415.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

What is claimed is:

1. A handheld laser treatment apparatus, wherein the apparatus comprises:
a handset including a treatment chamber, the treatment chamber having an open treatment aperture and a closed bottom of the treatment chamber; a laser array in the closed bottom arranged to project laser energy out from the treatment chamber to outside the treatment chamber through the open treatment aperture; and a pre-cooled circulating liquid coolant circuit within the handset; and,
an attachment, the attachment comprising a distal end and a proximal end;
the attachment being arranged for insertion into the open treatment aperture, the attachment including an optical element mounted at the distal end of the attachment;
the attachment being open from the proximal end to the distal end so that the optical element in the attachment proximal end receives laser energy projected by the laser array in the treatment chamber and transmits light to the distal end when inserted in the chamber, the optical element thereby accumulating thermal energy from projected laser energy;
the attachment further comprising a closed liquid circulating system comprising one or more liquid delivery channels within the attachment and around the optical element and a heat exchange interface coupled to the one or more liquid delivery channels;
the heat exchange interface being couplable to the pre-cooled circulating liquid coolant circuit in the handset;
wherein, when coupled, heat generated in the liquid within the closed liquid circulating system within the attachment due to accumulating thermal energy is absorbed by the pre-cooled circulating liquid coolant circuit through the heat exchange interface.

2. The apparatus of claim 1, further comprising a base unit operatively connected to the handset through an umbilical connection, the base unit including a cooling unit for receiving and cooling circulating liquid coolant to produce the pre-cooled circulating liquid coolant within the handset.

3. The apparatus of claim 1, wherein the optical element is an optical condenser adapter.

4. The apparatus of claim 3, wherein the optical condenser adapter comprises:
an adapter interface compatible with insertion into the treatment chamber of the handset, the adapter interface including an input aperture; a first optical member positioned at the input interface;
a second optical member at an output aperture of the optical condenser adapter; wherein the first optical member is arranged to receive parallel beams of laser light generated from the laser array and shift a path of optical energy of the laser light to concentrate at the second optical member.

5. The apparatus of claim 4, wherein the second optical member is arranged to further shift the path of optical energy received from the first optical member to produce parallel beams of laser light from the output aperture.

6. The apparatus of claim 4, wherein one or both of the first optical member and the second optical member are Fresnel lens elements.

7. The apparatus of claim 4, wherein the output aperture is smaller than the input aperture.

8. The apparatus of claim 4, wherein the output aperture is shaped as a polygon, circle, or ellipse, or a combination thereof.

* * * * *